(12) United States Patent
Spangler et al.

(10) Patent No.: US 11,055,380 B2
(45) Date of Patent: Jul. 6, 2021

(54) ESTIMATING THE PROBABILITY OF MATRIX FACTORIZATION RESULTS

(71) Applicant: INTERNATIONAL BUSINESS MACHINES CORPORATION, Armonk, NY (US)

(72) Inventors: William Scott Spangler, San Jose, CA (US); Katherine Shen, New York, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 145 days.

(21) Appl. No.: 16/186,182

(22) Filed: Nov. 9, 2018

(65) Prior Publication Data
US 2020/0151301 A1 May 14, 2020

(51) Int. Cl.
| | | |
|---|---|---|
| *G06F 17/00* | (2019.01) | |
| *G06F 17/16* | (2006.01) | |
| *G06F 16/23* | (2019.01) | |
| *G06F 16/28* | (2019.01) | |
| *G06F 16/2457* | (2019.01) | |
| *G16C 20/30* | (2019.01) | |
| *G16C 20/70* | (2019.01) | |

(52) U.S. Cl.
CPC .............. *G06F 17/16* (2013.01); *G06F 16/23* (2019.01); *G06F 16/24578* (2019.01); *G06F 16/288* (2019.01); *G16C 20/30* (2019.02); *G16C 20/70* (2019.02)

(58) Field of Classification Search
CPC .. G06F 16/23; G06F 16/24578; G06F 16/288; G16C 20/30; G16C 20/70
See application file for complete search history.

(56) References Cited

U.S. PATENT DOCUMENTS

| | | |
|---|---|---|
| 7,788,264 B2 | 8/2010 | Zhu et al. |
| 7,849,126 B1 | 12/2010 | Gonzalez et al. |

(Continued)

OTHER PUBLICATIONS

Wen Zhang, et al., "Feature-Derived Graph Regularized Matrix Factorization for Predicting Drug Side Effects," Neurocomputing 287 (2018) pp. 154-162.

(Continued)

*Primary Examiner* — Diedra McQuitery
(74) *Attorney, Agent, or Firm* — F. Chau & Associates, LLC

(57) ABSTRACT

A method for ranking a relationship between drugs and adverse events includes creating a matrix of associations between a plurality of drugs and a plurality of adverse events and factoring the matrix of associates into a pair of matrix factors. The matrix factors, when multiplied, approximate the matrix of associations, and a product of the matrix factors is a matrix of observed scores. The method further includes determining, for each drug and adverse event pair in the matrix of observed scores, a z-score, an expected score for each drug and adverse event pair, and a standard deviation for each drug and adverse event pair, calculating a probability of a relationship between a drug and adverse event using the z-score for the drug and adverse event pair, and determining that the drug and adverse event are related, when the probability of a relationship is greater than a predetermined magnitude.

12 Claims, 4 Drawing Sheets

(56) References Cited

U.S. PATENT DOCUMENTS

| | | | |
|---|---|---|---|
| 9,058,303 B2 | 6/2015 | Bouchard et al. | |
| 9,103,834 B2 | 8/2015 | Hood et al. | |
| 10,025,774 B2 | 7/2018 | Coulet et al. | |
| 2003/0211486 A1* | 11/2003 | Frudakis | C12Q 1/6883 |
| | | | 435/6.16 |
| 2007/0275399 A1* | 11/2007 | Lathrop | G16B 45/00 |
| | | | 435/6.14 |
| 2008/0235216 A1 | 9/2008 | Ruttenberg | |
| 2010/0169158 A1 | 7/2010 | Agarwal et al. | |
| 2013/0226616 A1* | 8/2013 | Nigam | G06Q 10/00 |
| | | | 705/3 |
| 2016/0140327 A1* | 5/2016 | Hu | G16H 50/50 |
| | | | 702/30 |
| 2019/0364063 A1* | 11/2019 | Lee | H04L 63/1416 |

OTHER PUBLICATIONS

Daniel D. Lee, et al, "Learning the Parts of Objects by Non-Negative Matrix Factorization," Nature, vol. 401, Oct. 21, 1999, pp. 788-791.

Liang-Chin Huang, et al., "Predicting Adverse Side Effects of Drugs," BMC Genomics, 2011, 12, (Suppl 5); pp. 1-10.

* cited by examiner

Table of AUC Results

| | |
|---|---|
| Agranulocytosis | 0.7903 |
| Aplastic anemia | 0.8621 |
| Erythema multiforme | 0.7046 |
| Hemolytic anemia | 0.8292 |
| Pancytopenia | 0.8859 |
| Pulmonary fibrosis | 0.6862 |
| Rhabdomyolysis | 0.7080 |
| Thrombotic thrombocytopenic purpura | 0.7635 |
| Toxic epidermal necrolysis | 0.7619 |
| AVERAGE AUC | 0.7769 |

FIG. 2

ESTIMATING THE PROBABILITY OF MATRIX FACTORIZATION RESULTS

TECHNICAL FIELD

Embodiments of the present disclosure are directed to methods of matrix factorization within a network of drug adverse event relationships for drug-adverse event prediction.

DISCUSSION OF THE RELATED ART

Almost all drugs have side effects, and unintended side effects can harm patients and lead to serious medical consequences. According to the U.S. Food and Drug Administration (FDA), up to 90% of all experimental drug compounds going through clinical trials fail to gain FDA approvals due to problems. Therefore, identifying drug side effects is important. Recent research on the adverse side effects of drugs in cells has shown that the traditional "one drug, one target, and causal effect" model is inadequate. Modern drugs are designed to regulate the functions of specific target proteins. Effective drugs can break through human barriers of absorption, discretion, metabolism, and excretion to achieve desirable effects. However, drugs may also bind to off-target proteins, potentially leading to unwanted side effects, which range from mild drowsiness to toxic. There need to be more appropriate models that take advantage of complex molecular responses of drugs in cells, by fully exploiting the relationships between chemical compounds, protein targets, and side effects observed at the physiological level.

The ranking and prioritization of potential relationships between entities is an important capability in many use cases. For example, in the life sciences this includes the ranking of drug targets to pursue for a given disease, or ranking of adverse events a drug may cause. Adverse drug reactions, especially those which are Designated Medical Events (DMEs), are a serious concern for patients, physicians, regulatory authorities, pharmaceutical companies, drug safety professionals and pharmacoepidemiologists. A number of methods have been employed to try and predict drug-adverse event (AE) associations, but those methods do not tap into hidden underlying patterns in literature text for their predictions.

Since laboratory methods of screening drugs is costly and time consuming, computational methods have been developed. Traditional methods use the structure-activity relationship or the structure-property relationship to make predictions. However, these methods identify drug side effects case by case, and are not suitable for analyzing complex data.

A network of connections between entities can be represented as a sparse matrix containing zeros where no connection exists between row/column entities and non-zeros whose magnitude indicate a relative strength of a relationship between row/column entities. Matrix factorization is a computational technique for collaborative filtering that creates a dense matrix from this sparse matrix by creating two product matrices which, when multiplied, approximate the original network. Matrix factorization has been employed as a ranking technique for drug discovery for uses such as prioritizing drug targets.

However, the raw scores generated by matrix factorization do not always correspond to the relative likelihood or interestingness of the relationship. For example, two entities that are highly connected in a network may receive a high score even though they are unrelated. Having a way to estimate the probability of a matrix factorization result for a given relationship by random chance would help in determining how interesting the result is in predicting potential outcomes. In addition, a common issue in ranking is determining a useful cutoff, a threshold above which it is worth committing the time and money to pursue a potential drug target in the lab, or thoroughly evaluate potential causality between a drug and an adverse event. Probability scores naturally lend themselves to cutoffs that are relatable to real world outcomes.

SUMMARY

Exemplary embodiments of the present disclosure are directed to systems and methods for solving the task of useful ranking, interpretation and determining a threshold for supporting businesses in deciding whether to commit resources to a task. Embodiments of the disclosure can provide a method to estimate an expected score and standard deviation needed to calculate a Z-score. The Z-score can be interpreted to tell how many standard deviations above or below an expected score is a raw score. From Z-scores, probabilities can be calculated and used as a threshold. Embodiments of the disclosure enable a user to estimate the expected value and standard deviation of a matrix factorization score. This enables the user to understand how unusual the observed value is, which gives them a sense of how "interesting" it is.

According to an embodiment of the disclosure, there is provided a computer-implemented method for ranking a relationship between entities. The method includes creating, by a computer, a matrix of associations between two or more types of entities, factorizing, by the computer, the matrix to produce an observed score, calculating, by the computer, a z-score, and determining, by the computer, that entities are related, using the z-score. The associations between two or more entity types are derived from unstructured data sources using natural language processing.

According to a further embodiment of the disclosure, factorizing the matrix further comprises utilizing a matrix factorization technique to output a raw score for every entity type being ranked.

According to a further embodiment of the disclosure, the z-score is calculated from an observed score, an expected score, and a standard deviation.

According to a further embodiment of the disclosure, the method includes calculating an area under a normal distribution curve using the z-score as an upper limit to determine the relationship between the two or more types of entities.

According to another embodiment of the disclosure, there is provided a computer-implemented method for ranking a relationship between drugs and adverse events. The method includes creating, by a computer, a matrix of associations between a plurality of drugs and a plurality of adverse events, factoring, by the computer, the matrix of associates into a pair of matrix factors, wherein the matrix factors, when multiplied, approximate the matrix of associations, wherein a product of the matrix factors is a matrix of observed scores, determining, by the computer, a z-score for each drug and adverse event pair in the matrix of observed scores from the matrix of observed scores, an expected score for each drug and adverse event pair, and a standard deviation for each drug and adverse event pair, calculating, by the computer, a probability of a relationship between a drug and adverse event using the z-score for the drug and adverse event pair, and determining, by the computer, that the drug and adverse event are related, when the probability of a relationship is greater than a predetermined magnitude.

According to a further embodiment of the disclosure, the matrix of associations is derived from unstructured data sources using natural language processing techniques.

According to a further embodiment of the disclosure, the matrix of associations is derived from structured data sources.

According to a further embodiment of the disclosure, the matrix of associations C is a binary matrix, wherein the expected score M(i, j) for drug i and adverse event j is $$M(i, j) = \frac{\sqrt{|row(i)|} + \sqrt{|column(j)|}}{\sqrt{|agents|} + \sqrt{|trgts|}},$$

where $\sqrt{|row(i)|} = \sqrt{\sum_{j=1}^{m} C(i,j)}$ and m is a number of adverse events, $\sqrt{|column(j)|} = \sqrt{\sum_{i=1}^{n} C(i,j)}$ and n is a number of drugs, |trgts|=number of 'adverse agents', |agents|=number of 'drugs', wherein the standard deviation SD(i, j) for drug i and adverse event j is $$SD(i, j) = M(i, j) \times \frac{\sqrt{|row(i)|} + \sqrt{|column(j)|}}{\sqrt{|row(i)| \times |column(j)|}},$$

and where the z-score Zscore(i,j) for drug i and adverse event j is $$Zscore(i, j) = \frac{O(i, j) - M(i, j)}{SD(i, j)},$$

where O(i,j) is the observed score for drug i and adverse event j.

According to a further embodiment of the disclosure, the matrix of associations C is a non-binary matrix. The expected score M(i, j) for drug i and adverse event j is $$M(i, j) = \frac{Coef \times \left(\sqrt{|row(i)|} + \sqrt{|column(j)|}\right)}{\sqrt{|agents|} + \sqrt{|trgts|}},$$

where $$Coef = \frac{\sum_{i=1, j=1}^{n,m} \sqrt{C(i, j)^2}}{Count},$$

Count=m×n, the number of cells in matrix C, $\sqrt{|row(i)|} = \sqrt{\sum_{j=1}^{m} C(i,j)^2}$, and $\sqrt{|column(j)|} = \sqrt{\sum_{i=1}^{n} C(i,j)^2}$.

According to another embodiment of the disclosure, there is provided a computer program product for ranking a relationship between drugs and adverse events, comprising a non-transitory program storage device readable by a computer, tangibly embodying a program of instructions executed by the computer to cause the computer to perform the method.

BRIEF DESCRIPTION OF THE DRAWINGS

FIG. 2 is a table of results of a matrix factorization for drug-AE prediction according to an embodiment of the disclosure.

DETAILED DESCRIPTION OF EXEMPLARY EMBODIMENTS

Figure 1:
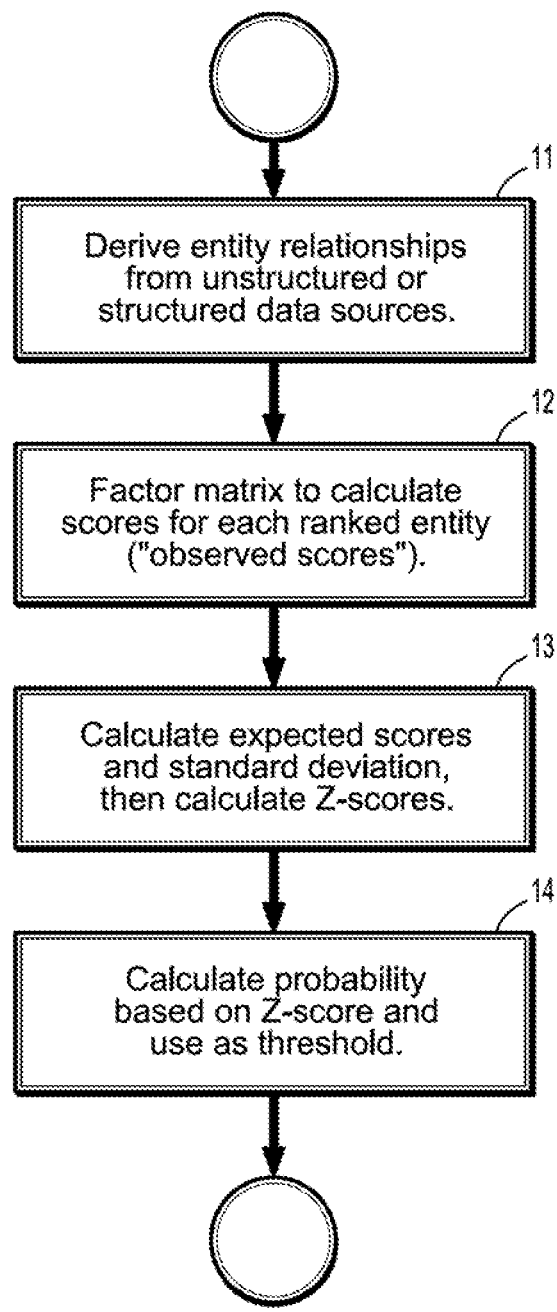
FIG. 1 is a flowchart of a method according to an embodiment of the disclosure.

Exemplary embodiments of the disclosure as described herein generally provide methods of matrix factorization for drug-adverse event prediction. While embodiments are susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

Embodiments of the disclosure can provide an estimation of an expected score and standard deviation for any given cell in a matrix, as part of calculating a Z-score from a matrix factorization analysis result. According to an embodiment, a modeling approach is used to generate the expected score and standard deviation. It is possible to estimate the expected score and standard deviation by generating mock entities with random relationships for the matrix. However, when the matrix is large, a very large sample size may be required, making that approach too expensive in terms of processing power to do at runtime. Embodiments of the disclosure can circumvent this issue while producing a similar result, by estimating the mean and standard deviation based on an equation, instead of sampling.

FIG. 1 is a flowchart of a method according to an embodiment of the disclosure. Referring now to the figure, a method according to an embodiment includes a matrix creation phase 11, an MF ranking phase 12, an MF Z-score calculation phase 13, and a probability determination phase 14.

A matrix creation phase 11 according to an embodiment is directed to the creation of a matrix of associations or relationships. The relationships are between two entity types, such as drugs and adverse events. The relationships can be derived from unstructured data sources, for example by using natural language processing techniques on a corpus of literature, or from structured data sources, such as from a table of drug-adverse event relationships in a drug database. The output of this phase is an m×n matrix C of relationships where m denotes the number of columns for one entity type, and n denotes the number of rows for the other entity type. The value of any given cell in the m×n matrix represents the known degree of association between those two entities.

A matrix factorization (MF) ranking phase 12 according to an embodiment is directed to the factorization of the matrix C from the previous phase such that the two resulting matrices, A and B, when multiplied, approximate the original matrix, i.e., A×B=O≈C. Matrix factorization techniques are known in the art. Matrix-factorization method known in the art include the singular value decomposition, the non-negative matrix factorization, and the probabilistic matrix factorization. Using a matrix factorization technique, an output of raw scores, also referred to herein as "observed scores", is generated for every entity being ranked.

A matrix factorization (MF) Z-score calculation phase 13 according to an embodiment is directed to the calculation of Z-scores. To calculate a Z-score, three components are used: (1) the observed score, obtained from the preceding phase's output, (2) an expected score, and (3) a standard deviation. Embodiments of the disclosure are directed to the calculation of the expected score and standard deviation, and are described separately below.

A probability determination phase 14 according to an embodiment is directed to the calculation of probabilities from Z-scores. For example, a p-value can be calculated using integration to find an area under a normal distribution curve, where the Z-score corresponds to the upper limit, using statistical analytics programs. The common thresholds of a p-value–0.05 or a p-value<0.01 can be used to determine which ranked entities may be worth pursuing for a business. The P-values are set low to avoid finding too many coincidences.

Calculating the Expected Score and Standard Deviation

According to an embodiment, an expected value of any given cell in a matrix is related to: (1) the dimensions of the input matrix (m×n); (2) the magnitude of the cell's column; and (3) the magnitude of the cell's row. The standard deviation is related to the expected value, and can be calculated based in part on the expected value.

For binary matrices, the following approximations hold:

$$C(i,j) \approx \sqrt{|column(j)|} = \sqrt[n]{\Sigma_{i=1}^{n} C(i,j)};$$

$$C(i,j) \approx \sqrt{|row(i)|} = \sqrt[m]{\Sigma_{j=1}^{m} C(i,j)};$$

$$C(i,j) \approx 1/\sqrt{|trgts|}; \text{ and}$$

$$C(i,j) \approx 1/\sqrt{|agents|},$$

where:
C(i,j)=value of the cell at position i, j in the original matrix from step 11;
|column(j)|=magnitude of column j;
|row(j)|=magnitude of row i;
|trgts|=magnitude of 'targets', one of the matrix dimensions, e.g., n; and
|agents|=magnitude of 'agents', the other matrix dimension, e.g., m.

Consequently, according to an embodiment, for binary matrices, the following expression can be used to calculate the expected score:

$$\text{Estimated}(i,j) = \frac{\sqrt{|row(i)|} + \sqrt{|column(j)|}}{\sqrt{|agents|} + \sqrt{|trgts|}}.$$

Depending on a precise use case, it can be useful to use a non-binary matrix, such as one that takes into account a "document support value", the number of literature documents supporting a particular relationship between two entities. Note that for a non-binary matrix, in the top two approximations for C(i,j), the C(i,j) under the radical would be replaced by C(i,j)². According to an embodiment, for these non-binary matrices, the following adjustment can be used:

$$\text{Coef}(\text{Matrix}) = \frac{\sum_{i=1,j=1}^{n,m} \sqrt{C(i,j)^2}}{\text{Count}},$$

where Count=n×m, the number of cells in the matrix. Thus, according to an embodiment, for a non-binary matrix, an expected score, standard deviation, and Z-score for a given cell can be calculated as follows:

$$\text{Expected score} = M(i,j) = \frac{\text{Coef} \times (\sqrt{|row(i)|} + \sqrt{|column(j)|})}{\sqrt{|agents|} + \sqrt{|trgts|}};$$

$$\text{Standard deviation} = SD(i,j) = M(i,j) \times \frac{\sqrt{|row(i)|} + \sqrt{|column(j)|}}{\sqrt{|row(i)| \times |column(j)|}}; \text{ and}$$

$$Zscore(i,j) = \frac{O(i,j) - M(i,j)}{SD(i,j)}.$$

According to an embodiment, a cognitive analytics platform containing a relationship network was used for the first phase of the embodiment described in FIG. 1. Using analytics, a matrix was created for drug-condition relationships, in which the conditions include adverse events. Matrix factorization was used to calculate raw (observed) scores for each drug's predicted association with a specified adverse event. Using a method according to an embodiment, expected scores, standard deviations, and Z-scores were calculated for each ranked drug.

EXPERIMENTAL EXAMPLE

An embodiment of the disclosure was used to predict potential drug-AE associations to support prioritization of AE reports in safety signal evaluation.

According to an embodiment, a matrix factorization (MF) within a network of drug and AE relationships was used for the drug-AE prediction. The network relationships were derived through natural language processing on Medline abstracts and PubMed Central Open Access (PMCOA) articles. Matrix factorization is a computational technique for collaborative filtering that creates a dense matrix from a sparse one by creating two product matrices which when multiplied approximate the original network. It is commonly used in recommender systems, e.g. suggesting movies to watch, but has not been employed in drug safety.

9 AE types were selected from the 2016 EMA DME list [Designated Medical Event (DME) list. European Medicines Agency; 2016. Available from: http://www.ema.europa.eu/docs/en_GB/document_library/Other/2016/08/WC500212079.xls] that were also included in the 2016 FDA DME list [2016 FDA OSE DMEs and Associated MedDRA Preferred Terms. US Food and Drug Administration; 2016. Available from: https://www.accessdata.fda.gov/drugsatfda_docs/nda/2016/206843Orig1s001,s003OtherR.pdf] and for which a single term was considered likely to capture the majority of events. These AE types are listed in the table of FIG. 2. Medications that included the selected DME in both the Warnings & Precautions section and ADR section of the drug label, but not in the Indications section, were selected as positive controls for MF scoring using known prescribing information analytics software on both US and UK medications. Negative controls for MF scoring were medications where the selected DME did not appear in any part of the label. The positive drug-AE pairs were zeroed out (removed)

from the input matrix and then the matrix was factored to yield a drug-AE score. From these observed scores, Z-scores were calculated using a simulated expected score and standard deviation for each pair. The Z-scores were then used to create a ranking of the drugs for a given DME.

An area under the receiver operator curve (AUC) was calculated to determine the accuracy of that ranking. This is the standard way to deal with situations where there are only a few True Positives and many True Negatives. A receiver operator curve considers the overall prevalence of True Positives in the data and the ranking of each True Positive in an overall ranking to determine how accurate the data is. A model according to an embodiment achieved an average AUC of 0.78 over the 9 DMEs. Note that a random ranking would measure an AUC=0.5. On average for a given DME, the mean true positive Z-score was 2.97 and the mean true negative Z-score was −1.35. The results are displayed in the table of FIG. 2. Based on these results, matrix factorization of DME-drug pairs according to embodiments shows promise as a useful tool in supporting safety signal triage and warrants further evaluation with other drug-AE pairings and in prospective studies.

System Implementations

It is to be understood that embodiments of the present disclosure can be implemented in various forms of hardware, software, firmware, special purpose processes, or a combination thereof. In one embodiment, an embodiment of the present disclosure can be implemented in software as an application program tangible embodied on a computer readable program storage device. The application program can be uploaded to, and executed by, a machine comprising any suitable architecture. Furthermore, it is understood in advance that although this disclosure includes a detailed description on cloud computing, implementation of the teachings recited herein are not limited to a cloud computing environment. Rather, embodiments of the present disclosure are capable of being implemented in conjunction with any other type of computing environment now known or later developed. An automatic troubleshooting system according to an embodiment of the disclosure is also suitable for a cloud implementation.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load balancing between clouds).

A cloud computing environment is service oriented with a focus on statelessness, low coupling, modularity, and semantic interoperability. At the heart of cloud computing is an infrastructure comprising a network of interconnected nodes.

Figure 3:
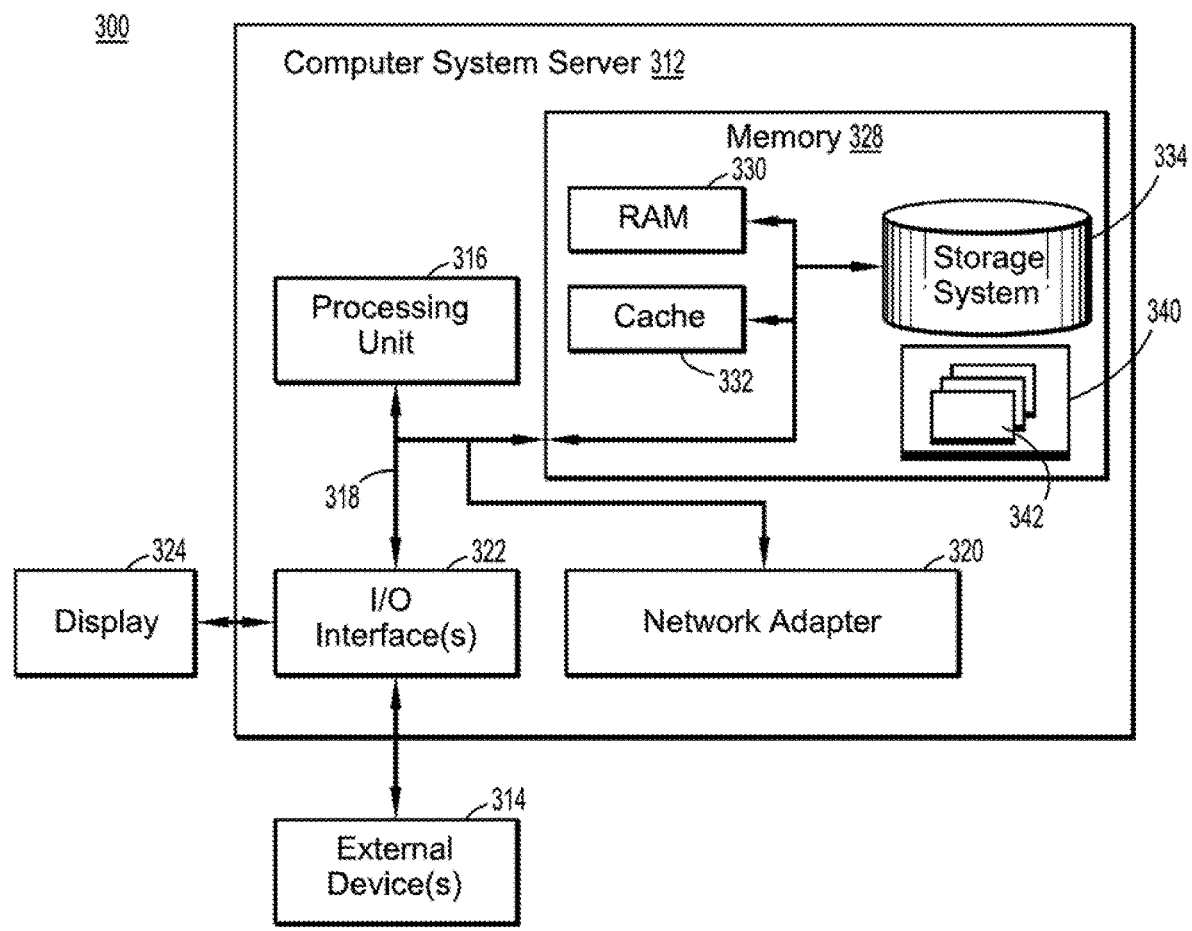
FIG. 3 is a schematic of an exemplary cloud computing node that implements an embodiment of the disclosure.

Referring now to FIG. 3, a schematic of an example of a cloud computing node is shown. Cloud computing node 310 is only one example of a suitable cloud computing node and is not intended to suggest any limitation as to the scope of use or functionality of embodiments of the disclosure described herein. Regardless, cloud computing node 310 is capable of being implemented and/or performing any of the functionality set forth herein above.

In cloud computing node 310 there is a computer system/server 312, which is operational with numerous other general purpose or special purpose computing system environments or configurations. Examples of well-known computing systems, environments, and/or configurations that may be suitable for use with computer system/server 312 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 312 may be described in the general context of computer system executable instructions, such as program modules, being executed by a computer system. Generally, program modules may include routines, programs, objects, components, logic, data structures, and so on that perform particular tasks or implement particular abstract data types. Computer system/server 312 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 3, computer system/server 312 in cloud computing node 310 is shown in the form of a general-purpose computing device. The components of computer system/server 312 may include, but are not limited to, one or more processors or processing units 316, a system memory 328, and a bus 318 that couples various system components including system memory 328 to processor 316.

Bus 318 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 312 typically includes a variety of computer system readable media. Such media may be any available media that is accessible by computer system/server 312, and it includes both volatile and non-volatile media, removable and non-removable media.

System memory 328 can include computer system readable media in the form of volatile memory, such as random access memory (RAM) 330 and/or cache memory 332. Computer system/server 312 may further include other removable/non-removable, volatile/non-volatile computer system storage media. By way of example only, storage system 334 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 418 by one or more data media interfaces. As will be further depicted and described below, memory 328 may include at least one program product having a set (e.g., at least one) of program modules that are configured to carry out the functions of embodiments of the disclosure.

Program/utility 340, having a set (at least one) of program modules 342, may be stored in memory 328 by way of example, and not limitation, as well as an operating system, one or more application programs, other program modules, and program data. Each of the operating system, one or more application programs, other program modules, and program data or some combination thereof, may include an implementation of a networking environment. Program modules 342 generally carry out the functions and/or methodologies of embodiments of the disclosure as described herein.

Computer system/server 312 may also communicate with one or more external devices 314 such as a keyboard, a pointing device, a display 324, etc.; one or more devices that enable a user to interact with computer system/server 312; and/or any devices (e.g., network card, modem, etc.) that enable computer system/server 312 to communicate with one or more other computing devices. Such communication can occur via Input/Output (I/O) interfaces 322. Still yet, computer system/server 312 can communicate with one or more networks such as a local area network (LAN), a general wide area network (WAN), and/or a public network (e.g., the Internet) via network adapter 320. As depicted, network adapter 320 communicates with the other components of computer system/server 312 via bus 318. It should be understood that although not shown, other hardware and/or software components could be used in conjunction with computer system/server 312. Examples, include, but are not limited to: microcode, device drivers, redundant processing units, external disk drive arrays, RAID systems, tape drives, and data archival storage systems, etc.

Figure 4:
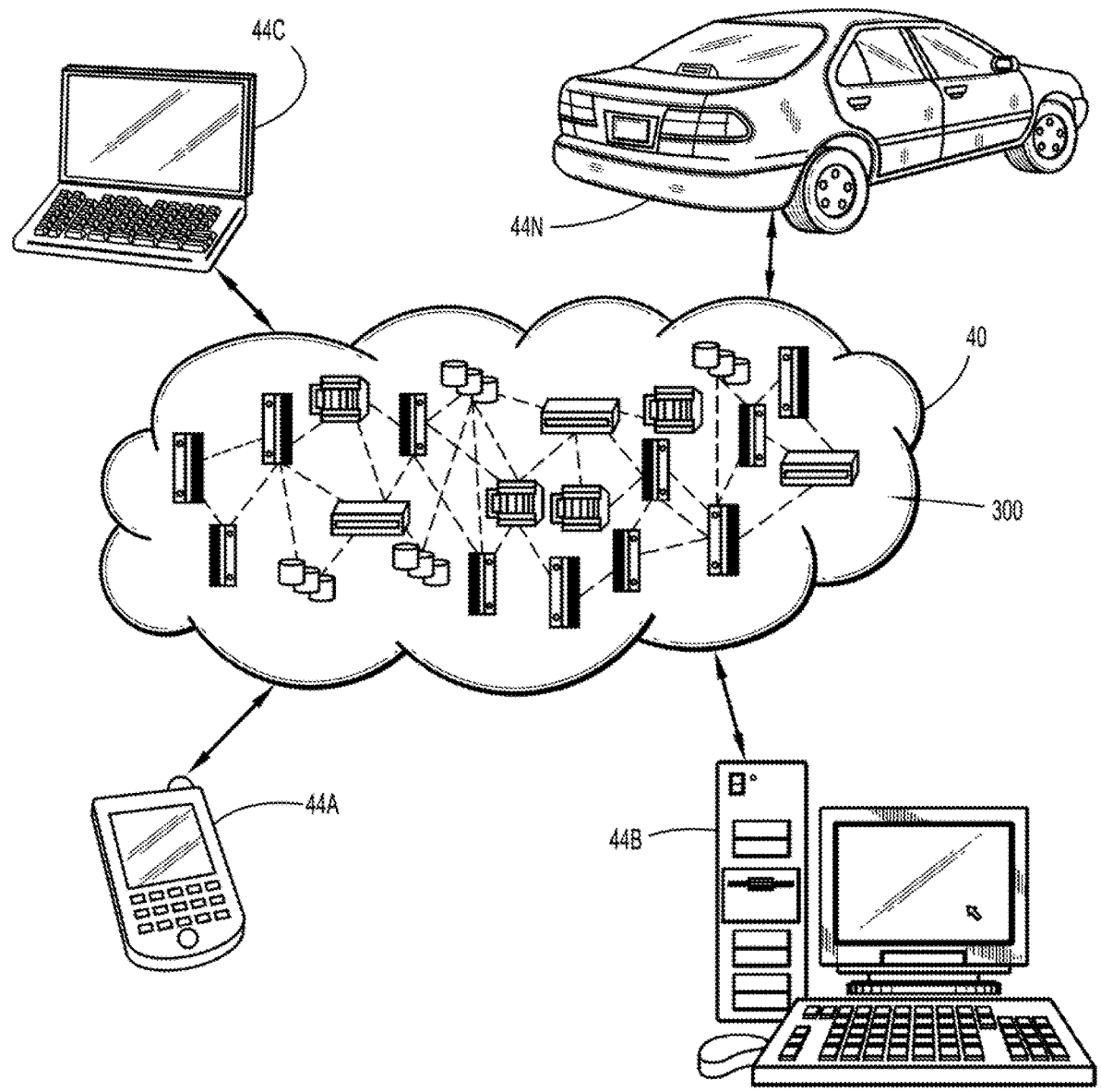
FIG. 4 shows an exemplary cloud computing environment according to embodiments of the disclosure.

Referring now to FIG. 4, illustrative cloud computing environment 40 is depicted. As shown, cloud computing environment 40 comprises one or more cloud computing nodes 300 with which local computing devices used by cloud consumers, such as, for example, personal digital assistant (PDA) or cellular telephone 44A, desktop computer 44B, laptop computer 44C, and/or automobile computer system 44N may communicate. Nodes 300 may communicate with one another. They may be grouped (not shown) physically or virtually, in one or more networks, such as Private, Community, Public, or Hybrid clouds as described hereinabove, or a combination thereof. This allows cloud computing environment 40 to offer infrastructure, platforms and/or software as services for which a cloud consumer does not need to maintain resources on a local computing device. It is understood that the types of computing devices 44A-N shown in FIG. 4 are intended to be illustrative only and that computing nodes 300 and cloud computing environment 40 can communicate with any type of computerized device over any type of network and/or network addressable connection (e.g., using a web browser).

While embodiments of the present disclosure has been described in detail with reference to exemplary embodiments, those skilled in the art will appreciate that various modifications and substitutions can be made thereto without departing from the spirit and scope of the disclosure as set forth in the appended claims.

What is claimed is:

1. A computer-implemented method for ranking a relationship between drugs and adverse events, the method comprising:
creating, by a computer, a matrix of associations between a plurality of drugs and a plurality of adverse events using a matrix factorization modeling approach, wherein the matrix contains zeros where no connection exists between row/column entities and non-zeros whose magnitude indicate a relative strength of a relationship between row/column entities;
the matrix factorization modeling approach comprising:
factoring, by the computer, the matrix of associates into a pair of matrix factors, wherein the matrix factors, when multiplied, approximate the matrix of associations, wherein a product of the matrix factors is a matrix of observed scores;
determining, by the computer, a z-score for each drug and adverse event pair in the matrix of observed scores from the matrix of observed scores, an expected score for each drug and adverse event pair, and a standard deviation for each drug and adverse event pair;
calculating, by the computer, a probability of a relationship between a drug and adverse event using the z-score for the drug and adverse event pair;
determining, by the computer, that the drug and adverse event are related, when the probability of a relationship is greater than a predetermined non-negative number; and
ranking those drug and adverse event that are related and screening drugs that are related to adverse events using the rankings, wherein the rankings of the drugs and adverse events are used to effect treatments for medical conditions,
wherein the matrix of associations C is a binary matrix, wherein the expected score $M(i, j)$ for drug i and adverse event j is $$M(i, j) = \frac{\sqrt{|row(i)|} + \sqrt{|column(j)|}}{\sqrt{|agents|} + \sqrt{|trgts|}}$$

wherein $$\sqrt{|row(i)|} = \sqrt{\sum_{j=1}^{m} C(i, j)}$$

wherein m is a number of adverse events, $$\sqrt{|column(j)|} = \sqrt{\sum_{i=1}^{n} C(i, j)}$$

wherein n is a number of drugs,
|trgts|=number of 'adverse events',
|agents|=number of 'drugs',
wherein the standard deviations $SD(i, j)$ for drug i and adverse event j is $$SD(i, j) = M(i, j) \times \frac{\sqrt{|row(i)|} + \sqrt{|column(j)|}}{\sqrt{|row(i)|} \times \sqrt{|column(j)|}},$$

and
wherein z-score $Zscore(i,j)$ for drug i and adverse event j is $$Zscore(i, j) = \frac{O(i, j) - M(i, j)}{SD(i, j)},$$

wherein $O(i,j)$ is the observed score for drug i and adverse event j.

2. The method of claim 1, wherein the matrix of associations is derived from unstructured data sources using natural language processing techniques.

3. The method of claim 1, wherein the matrix of associations is derived from structured data sources.

4. The method of claim 1, wherein the matrix of associations C is a non-binary matrix, and wherein the expected score $M(i, j)$ for drug i and adverse event j is $$M(i, j) = \frac{Coef(\sqrt{|row(i)|} + \sqrt{|column(j)|})}{\sqrt{|agents|} \times \sqrt{|trgts|}},$$

wherein $$Coef = \frac{\sum_{i=1, j=1}^{n,m} \sqrt{C(i, j)^2}}{Count},$$

Count=n×m, the number of cells in matrix C, $$\sqrt{|row(i)|} = \sqrt{\sum_{j=1}^{m} C(i, j)^2},$$

and $$\sqrt{|column(j)|} = c\sqrt{\sum_{i=1}^{n} C(i, j)^2}.$$

5. A computer program product for ranking a relationship between drugs and adverse events, comprising a non-transitory program storage device readable by a computer, tangibly embodying a program of instructions executed by the computer to cause the computer to perform a method comprising the steps of:
creating, by a computer, a matrix of associations between a plurality of drugs and a plurality of adverse events using a matrix factorization modeling approach, wherein the matrix contains zeros where no connection exists between row/column entities and non-zeros whose magnitude indicate a relative strength of a relationship between row/column entities;
the matrix factorization modeling approach comprising:
factoring, by the computer, the matrix of associates into a pair of matrix factors, wherein the matrix factors, when multiplied, approximate the matrix of associations, wherein a product of the matrix factors is a matrix of observed scores;

determining, by the computer, a z-score for each drug and adverse event pair in the matrix of observed scores from the matrix of observed scores, an expected score for each drug and adverse event pair, and a standard deviation for each drug and adverse event pair;

calculating, by the computer, a probability of a relationship between a drug and adverse event using the z-score for the drug and adverse event pair;

determining, by the computer, that the drug and adverse event are related, when the probability of a relationship is greater than a predetermined non-negative number; and ranking those drug and adverse event that are related and screening drugs that are related to adverse events using the rankings, wherein the rankings of the drugs and adverse events are used to effect treatments for medical conditions, wherein the matrix of associations C is a Unary matrix, wherein the expected score M(i, j) for drug i and adverse event j is $$M(i, j) = \frac{\sqrt{|row(i)|} + \sqrt{|column(j)|}}{\sqrt{|agents|} \times \sqrt{|trgts|}}$$

wherein $$\sqrt{|row(i)|} = \sqrt{\sum_{j=1}^{m} C(i, j)}$$

wherein m is a number of adverse events, $$\sqrt{|column(j)|} = \sqrt{\sum_{i=1}^{n} C(i, j)}$$

wherein n is a number of drugs,
|trgts|=number of 'adverse events',
|agents|=number of 'drugs',
wherein the standard deviation SD(i, j) for drug i and adverse event j is $$SD(i, j) = M(i, j) \times \frac{\sqrt{|row(i)|} + \sqrt{|column(j)|}}{\sqrt{|row(i)|} \times \sqrt{|column(j)|}},$$

and
wherein z-score Zscore(i,j) for drug i and adverse event j is $$Zscore(i, j) = \frac{O(i, j) - M(i, j)}{SD(i, j)},$$

wherein O(i,j) is the observed score for drug i and adverse event j.

6. The computer program product of claim 5, wherein the matrix of associations is derived from unstructured data sources using natural language processing techniques.

7. The computer program product of claim 5, wherein the matrix of associations is derived from structured data sources.

8. The computer program product of claim 5, wherein the matrix of associations C is a non-binary matrix, and wherein the expected score M(i, j) for drug i and adverse event j is $$M(i, j) = \frac{Coef \times \sqrt{|row(i)|} + \sqrt{|column(j)|}}{\sqrt{|agents|} \times \sqrt{|trgts|}},$$

wherein $$Coef = \frac{\sum_{i=1, j=1}^{n,m} \sqrt{C(i, j)^2}}{Count},$$

Count=n×m, the number of cells in matrix C, $$\sqrt{|row(i)|} = \sqrt{\sum_{j=1}^{m} C(i, j)^2},$$

and $$\sqrt{|column(j)|} = c\sqrt{\sum_{i=1}^{n} C(i, j)^2}.$$

9. The method of claim 1, wherein factorizing the matrix further comprises outputting a raw score for every entity type being ranked.

10. The method of claim 1, wherein calculating an area under a normal distribution curve uses the z-score as an upper limit to determine the relationship between the two or more types of entities.

11. The method of claim 5, wherein factorizing, the matrix further comprises outputting a raw score for every entity type being ranked.

12. The method of claim 5, wherein calculating an area under a normal distribution curve uses the z-score as an upper limit to determine the relationship between the two or more types of entities.

* * * * *